United States Patent [19]

McMahon et al.

[11] Patent Number: 5,356,785
[45] Date of Patent: Oct. 18, 1994

[54] IMMUNOASSAYS HAVING AT LEAST TWO TEST SPOTS AND REFERENCE SPOT

[75] Inventors: Philip McMahon, Falmouth; Larry Chaney; Quentin Tonelli, both of Portland, all of Me.

[73] Assignee: Idexx Laboratories, Inc., Westbrook, Me.

[21] Appl. No.: 700,068

[22] Filed: May 2, 1991

Related U.S. Application Data

[63] Continuation of Ser. No. 145,522, Jan. 19, 1988, abandoned.

[51] Int. Cl.$^5$ .......................................... G01N 33/543
[52] U.S. Cl. .................................. 435/7.92; 435/7.93; 435/967; 435/970; 435/975; 436/501; 436/518; 436/805; 436/809; 436/817
[58] Field of Search .................. 435/7.92, 7.93, 967, 435/970, 975; 436/501, 518, 805, 809, 817

[56] References Cited

U.S. PATENT DOCUMENTS

| | | | |
|---|---|---|---|
| 4,540,659 | 9/1985 | Litman et al. | 435/7 |
| 4,703,017 | 10/1987 | Campbell et al. | 436/530 |
| 4,912,034 | 3/1990 | Kalra et al. | 435/7 |
| 4,916,056 | 4/1990 | Brown, III et al. | 435/7 |

FOREIGN PATENT DOCUMENTS

| | | |
|---|---|---|
| 8770447 | 9/1987 | Australia . |
| 0093613 | 11/1983 | European Pat. Off. . |
| 0203238 | 12/1986 | European Pat. Off. . |
| 0217403 | 4/1987 | European Pat. Off. . |
| 0253464 | 1/1988 | European Pat. Off. . |
| 89300490 | 8/1990 | European Pat. Off. . |
| 8502466 | 6/1985 | PCT Int'l Appl. . |
| 2186078 | 8/1987 | United Kingdom . |

OTHER PUBLICATIONS

Chandler et al., "Monoclonal Hybridoma Antibodies against Human IgE and Their Use in a Rapid and Sensitive Enzyme Immunoassay for the Semiquantitative Assessment of Total IgE Levels in Human Blood", Int. Archs. Allergy appln. Immun. 72: 267–272 (1983).
Hybritech Advertisement.

*Primary Examiner*—David Saunders
*Attorney, Agent, or Firm*—Fish & Richardson

[57] ABSTRACT

In one aspect, a kit for the semi-quantitative measurement, in a liquid sample, by competitive immunoassay, of a first member of a specific binding pair, the kit including a solid support bearing

- a reference area which provides a detectable signal in the immunoassay, and
- a first and a second test area exposed to contact the sample, each test area containing a different amount of second or first member of the specific binding pair,
- whereby the intensity of the detectable signal from the reference area can be compared with the intensity of any detectable signals from the first and second test areas in the presence of an unknown quantity of the first member in the sample.

11 Claims, 3 Drawing Sheets

IMMUNOASSAYS HAVING AT LEAST TWO TEST SPOTS AND REFERENCE SPOT

This is a continuation of copending application Ser. No. 07/145,522 filed on Jan. 19, 1988 and now abandoned.

BACKGROUND OF THE INVENTION

This invention relates to immunoassay methods for the detection or measurement of substances in liquid samples, e.g., biological fluids such as whole blood, serum, plasma, and urine.

A wide variety of substances are commonly detected or measured by immunoassay methods in biological samples; examples are hormones, antibodies, toxins, and drugs. Usually, although not always, either the substance being detected, or a substance used in its detection, is an antibody, hence the term "immunoassay". The antibody is a member of a specific binding pair, the other member of the pair being referred as an antigen or analyte. Other specific binding pairs, besides antibody-antigen pairs, which are measured and used in immunoassays, include pairs of molecules which have specific binding affinity for each other, e.g., hormones—hormone receptors, and biotin-avidin.

Immunoassays are commonly carried out, at least in part, on solid supports, e.g., glass fiber membranes. The two most common formats for immunoassays employing solid supports are competitive and sandwich formats. In a typical competitive assay, the substance to be measured (the analyte) is a low molecular weight substance such as a drug residue or small hormone, with a molecular weight from about 100 to about 2,000; such low molecular weight substances do not easily lend themselves to sandwich assays, described below. In the typical competitive assay, an antibody to the analyte is immobilized on a solid support, and the sample suspected of containing the analyte is brought into contact with that solid support. At the same or a later time, a liquid solution containing labeled analyte is contacted with the support, so that the labeled analyte and any analyte in the sample compete for binding to the immobolized antibody. (If the substance being measured is itself an antibody, the immobilized analyte can be either antibody to that antibody, or an antigen for which that antibody is specific.) The solid support is then washed and the amount of label measured or detected as an inverse measure of analyte in the sample. Typically, the label is a chemiluminescent substance, a radioisotope, or, most preferably, an enzyme which, in the final step, reacts with a chromogenic substrate, which develops color of intensity inversely related to the amount of analyte present in the sample. A typical competitive format is described, e.g., in Litman et al. U.S. Pat. No. 4,540,659, hereby incorporated by reference. In the Litman et al. competitive assay, in addition to the test spot, the solid support also bears what Litman et al. refer to as a "calibration surface" which, preferably, but not necessarily, contains antibody to the substance being measured, and serves as "a standard for the evaluation for the signal level of the measurement surface" (column 3, lines 14 through 17).

Sandwich immunoassays (e.g., as described in David et al. U.S. Pat. No. 4,376,110, hereby incorporated by reference) generally are used to detect or measure substances (again, analytes) of molecular weights above 2,000, e.g., antibodies and other proteins. In a typical sandwich assay, a first antibody to the analyte is immobilized on a solid support, which is then contacted with the liquid sample so that any analyte in the sample binds to the antibody. A second, labeled antibody to the analyte is then added, the support is washed, and the amount of bound label is measured, bound label being proportional to the amount of analyte in the sample.

A goal of some immunoassays has been a result which is not simply a positive or negative, but which is semiquantitative, i.e., provides a rough, not totally precise estimate of the amount of analyte present in the sample. For example, Chandler et al., International Archives of Allergy and Applied Immunology 72, 267, 1983 describes a semiquantitative immunoassay for IgE in plasma employing three glass capillary tubes, each bearing immobilized antibody specific for IgE. Swanljung European Patent Application No. WO85/02466 describes a colorimetric immunoassay in which the test color is compared to reference colors to provide a semiquantative result. Litman et al., above, states that "one can quantitate the observed results in relation to ratios obtained with known amounts of the analyte and graphing the change in ratio of signal level with change in concentration."

SUMMARY OF THE INVENTION

There are a number of aspects of the present invention which provide immunoassays which are superior to prior assays in various ways.

In one aspect, the invention features a kit for the semiquantitative measurement, in a liquid sample, by competitive immunoassay, of a first member of a specific binding pair. The kit includes a solid support which bears a reference area which provides a detectable signal in the immunoassay, as well as a first and second test area, each of which contains a different amount of first or second member of the specific binding pair, whereby the intensity of the detectable signal from the reference area can be compared with the intensity of any detectable signals from the two test areas in the presence of an unknown quantity of the first binding pair member in the sample. The two amounts of binding pair member on the test areas are preferably selected so that the first area, but not the second area, generates a detectable signal of significantly lower intensity than that of the reference area (i.e., can be distinguished from the reference area by eye, without the need for instruments) when the sample contains a first amount of the first member of the specific binding pair, while both areas generate detectable signals significantly lower in intensity than that of the reference area when the sample contains a second, greater amount of the first member of the specific binding pair. Preferably, the intensity of the signal generated by the first test area varies in substantially linear fashion when the sample contains the first member of the specific binding pair in an amount within a first range, and the intensity of the signal generated by the second test area varies in substantially linear fashion when the sample contains the first member of the specific binding pair in an amount within a second, greater range. The two test areas are best able to exhibit this desired linear response to different ranges when the amounts of binding pair member in the test areas are selected so that the first test area is saturated when the sample contains the first member of the specific binding pair in a first amount and the second test area is not saturated at that first amount, but is saturated at a second, higher amount. If a wide range of amounts of the first member of the specific binding pair are of interest, the solid support can, of course, bear more than two test areas, each of which will, by virtue of its containing a different amount of binding pair member, have a different maximum binding capacity for the first member, and thus a different linear range.

The competitive test can have two configurations. In one, the support test areas bear second binding pair member (e.g., antibody or receptor protein), and labeled and sample first member compete for binding to test areas. In the second configuration, the test areas bear first binding member which competes with first binding member in the sample for binding to the labeled second binding member; first binding member in the sample binds labeled second member, decreasing its signal-producing binding to the test areas.

The competitive immunoassay of the invention provides semiquantitative results without the need to run standards and compare a test result to such standards. Furthermore, the assay enables the semiquantitative result to be obtained with only one addition of sample to the test apparatus, providing a simple, convenient test procedure. In addition, where, as is preferred, the label used is an enzyme, which reacts with a chromogenic substrate, the semiquantitative result can be read by eye, without the need for a radioisotope counter or other apparatus.

In another, related aspect, the invention provides a kit for the determination, by competitive immunoassay, of the presence in a liquid sample of an amount greater than or equal to a predetermined, physiologically significant amount of a first member of a specific binding pair. The kit includes a solid support which, like the support discussed in connection with the first aspect of the invention, above, bears a reference area which provides a detectable signal in the immunoassay, as well as a test area adapted to generate a detectable signal of lesser intensity with greater concentrations of first binding pair member in the sample, and containing the first or second member of the specific binding pair in an amount which, in the immunoassay, causes the test area to generate a detectable signal of significantly lower intensity than that of the reference area when the first member of the specific binding pair is present in the sample in an amount equal to or greater than a predetermined, physiologically significant amount, and which does not, in the immunoassay, cause the test area to generate a signal of significantly lower intensity from that of the reference area when the first specific binding member is present in the sample in an amount below that predetermined, physiologically significant amount. A signal which has a "significantly lower intensity" than that of the reference signal is one which can be detected visually by a human user of the test, without the use of measurement instruments. This aspect of the invention has the greatest utility in the detection of physiologically important threshhold levels of such substances as toxins and drugs, which might be harmless in small amounts and are of interest only if present in greater than a predetermined minimum amount. As in the multiple spot competitive test described above, the test area can bear either first or second binding pair member.

In both aspects of the invention, above, the kit preferably further includes labeled first or second member of the specific binding pair, depending on which binding pair member is immobilized in the test areas. Most preferably, labeling is by means of an enzyme which acts on a chromogenic substrate to produce a color change, and the reference area contains antibody to the enzyme, but does not contain any first or second member of the specific binding pair, and thus becomes colored in every test by virtue of the enzyme-labeled first or second binding pair member's binding to the anti-enzyme antibody in the reference area. Because the reference area does not contain the first or second member of the specific binding pair, its color change is independent of the amount of first specific binding member present in the sample. Further, the reference area provides control for batch to batch variations in enzyme and chromogenic substrate, because its color change, like the color changes of the test areas, is a product of the action of those reagents.

In another aspect, the invention provides a kit for the semiquantitative measurement in a liquid sample, by sandwich immunoassay, of an analyte, e.g., an antibody or other protein. The kit includes a solid support bearing a test area containing a first antibody specific for the analyte, and a first and second calibration area, each of which contains a different amount of the analyte being tested for, whereby the intensity of the detectable signal from the test area can be compared with the intensity of the detectable signal from the first and second calibration areas in the presence of an unknown quantity of analyte in the sample. Preferably the kit further includes a labeled second antibody specific for the analyte, so that, on the test area, a conventional labeled sandwich is formed when the analyte is present in the sample. The reference areas bind labeled antibody independently of the presence or level of analyte in the sample. Furthermore, each reference area, by virtue of its different amount of analyte, has a binding capacity for labeled antibody different from the others, and thus each is saturated at a different level. Thus, a semiquantitative result can be obtained; the test area is compared to the reference areas, each of which represents a range of analyte; it can thus be determined that the sample contains an amount of analyte in the range of the maximum binding capacity of the reference area which matches the test area. The sandwich assay of the invention is thus useful where it is important to know not simply whether an analyte is present in a sample, but to know its approximate quantity. This assay, like the above described competitive assay, permits this semiquantitative result to be obtained with the use of only one sample in one test kit apparatus.

In another aspect, the invention features an alternative kit for the semiquantitative measurement, in a liquid sample, by sandwich immunoassay, of an analyte. The kit includes a solid support bearing a first and a second test area, each of which contains a different amount of a first antibody specific for the analyte, whereby the presence in the sample of the analyte in a first amount causes a substantial change in signal intensity (development of a signal which is greater than 50% of the signal the test area could develop in the presence of unlimited analyte) in the first but not the second test area, and the presence in the sample of the analyte in a second, greater amount causes a substantial change in signal intensity in both first and second test areas. Preferably, the kit further includes an enzyme-labeled second antibody to the analyte.

Other features and advantages of the invention will be apparent from the following description of the preferred embodiments thereof, and from the claims.

DESCRIPTION OF THE PREFERRED EMBODIMENTS

The drawings will first briefly be described.

Drawings

COMPETITIVE IMMUNOASSAY APPARATUS

Figure 1A:
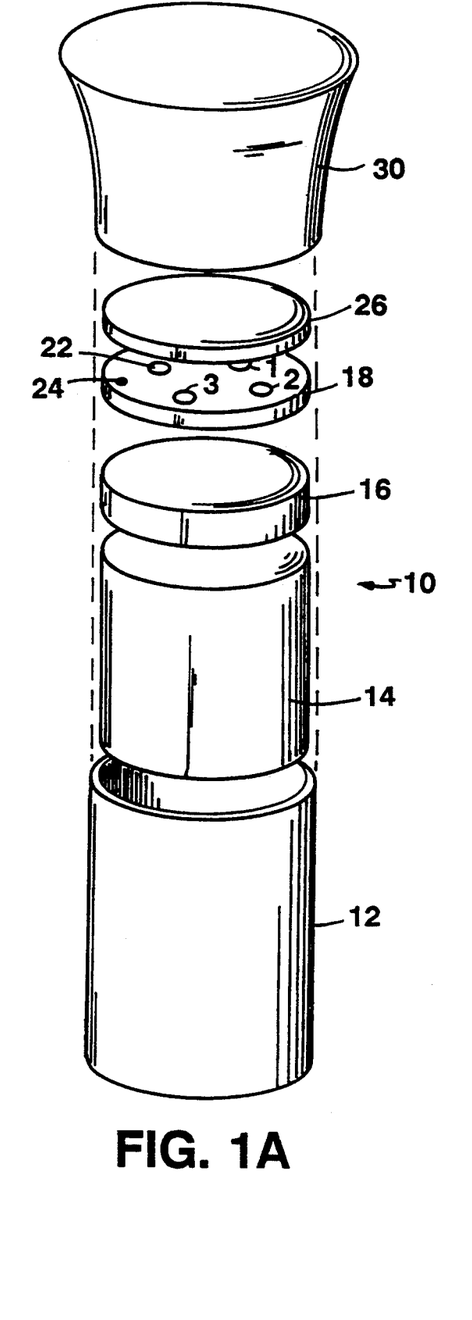
FIG. 1A is an exploded prospective view of apparatus for use of the invention.
Figure 1B:
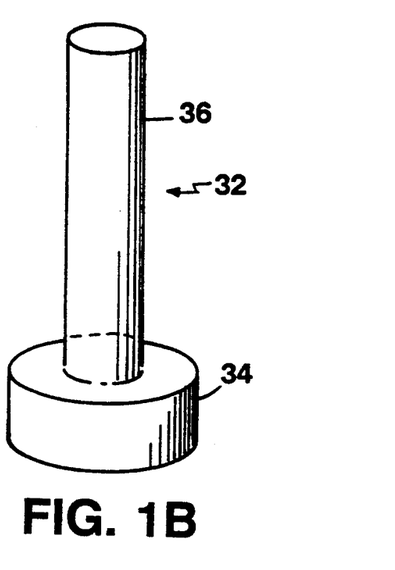
FIG. 1B is a view of a sponge means to be used with the apparatus of FIG. 1A.

Referring to FIGS. 1A and 1B, test apparatus 10 is generally of the configuration described in U.S. Pat. No. 4,376,110, hereby incorporated by reference. Apparatus 10, adapted for the measurement of progesterone in mare serum, includes plastic cup 12 in which there is placed plug 14, comprising absorbant material supplied by American Filtrona Corporation, supporting porous polyethylene disk 16, and glass fiber membrane 18 (pore size 1 micron, obtained from Gelman Sciences). Pre-filter 26 (the same as membrane 18) is positioned between test membrane 18 and plastic lid 30. Filter 26 is removable so that test results can be read on test membrane 18. Auxilliary to apparatus 10 is sponge means 32, comprising sponge plug 34 and handle 36. Sponge 32 serves the function of seating pre-wetted membrane 18 at the start of the assay.

Figure 2:
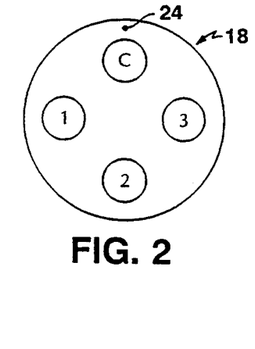
FIG. 2 is a diagrammatic representation of a solid support (18, FIG. 1) of the invention, for use in a competitive immunoassay, bearing a reference area and three test areas.

Referring to FIG. 2, membrane 18 bears reference spot C and, when a semiquantitative assay is to be carried out, multiple test spots 1, 2 and 3, each of which contains a different concentration of latex particles coated with anti-equine progesterone monoclonal antibody (Immunosearch, Toms River, N.J.). For loading, polystyrene latex particles are suspended in phosphate buffer containing the antibody, washed, and then resuspended in phosphate buffer for spotting onto membrane 18. Each antibody coated particle preparation, prior to spotting, is diluted with latex particles coated with the inert protein bovine serum albumin (BSA), so that the percent antibody particles on the spots are: spot 1, 40%; spot 2, 50%, and spot 3, 60%. The concentrations of antibody are selected such that spot 1 is saturated when the serum sample contains one ng/ml of progesterone, spot 2 is saturated at 5 ng/ml, and spot 3 is saturated at 10 ng/ml. Where the assay, rather than being semiquantitative (as defined above), is for the purpose of determining whether or not progesterone is present in a sample in an amount greater than a physiologically significant amount (e.g., 4 ng/ml); membrane 18 bears only one test spot, which undergoes significant color intensity change only when progesterone is present in the sample in an amount greater than that physiologically significant level. Reference spot C contains latex particles coated, as above, with antibody to the enzyme label, horseradish peroxidase (HRP) (Accurate Chemicals). Located above reference spot C is orientation dot 24. As an alternative to using latex particles, the antibodies can be spotted directly onto the membrane either passively adsorbed, or by chemical cross-linking.

Operation of Semiquantitative Competitive Assay

Referring again to FIGS. 1A and 1B., membrane 18 is pre-wetted with several drops of wash solution containing 0.25–1M sodium chloride, 2% dry milk, 5% bovine serum albumin, and preservatives. Ten to fifteen drops of serum are then applied to membrane 18 and allowed to react for five minutes to permit any progesterone present in the sample to bind to the antibody in test spots one, two, and three. Cap 30 and pre-filter 26 are then removed and wash solution is added, and then three to four drops of HRP-labeled progesterone (Sigma Chemical Co., St. Louis, Mo.) are added, this labeled analyte binds to any antibody on test spots one, two, and three not bound to progesterone in the sample. The labeled progesterone is allowed to react for one minute, the membrane is again washed with wash solution, and then three to four drops of the chromagenic substrate tetramethylbenzidine are added and allowed to react, developing color, for one minute. There are then added ten to fifteen drops of standard stop solution, completing the assay.

Figure 3A:
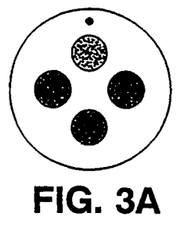
FIGS. 3A–3G are a diagrammatic representation of the response of the solid support of FIG. 2 to various concentrations a substance in a sample.
Figure 3B:
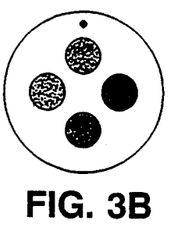
Figure 3C:
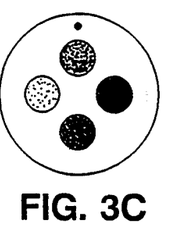
Figure 3D:
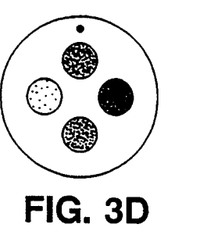
Figure 3E:
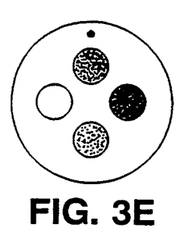
Figure 3F:
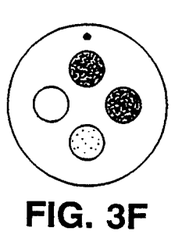
Figure 3G:
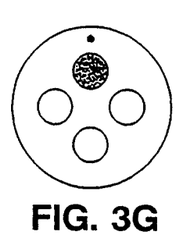

FIGS. 3A–3G illustrates the results of tests carried out with solutions containing four different, progressively greater concentrations of equine progesterone. In each of the seven membranes shown, spot C has undergone the same degree of color change, independently of the concentration of progesterone in the sample. In the membrane A of FIG. 3, treated with sample containing less than one unit (1 ng/ml) of progesterone, reference spot C is lighter than all three test spots. In the membrane of FIG. 3B, treated with sample containing one unit of progesterone, reference spot C exhibits the same color as test spot one, but is lighter than spots two and three. The membrane of FIG. 3C, treated with sample containing between one and five units of progesterone, shows spot C lighter than spots one and two but darker than spot three. In the membrane of FIG. 3D, treated with sample containing five units of progesterone, reference spot C has the same color intensity as spot two, is darker than spot one, and lighter than spot three. In the membrane of FIG. 3E, treated with sample containing between five and ten units of progesterone, spot C is darker than spot one and two but lighter than spot three. In the membrane of FIG. 3F, treated with sample containing ten units of progesterone, spot C is equal in intensity to spot three, but darker than spots one and two. In the membrane of FIG. 3F, treated with sample containing more than ten units of progesterone, spot C is darker than all three test spots.

Figure 4:
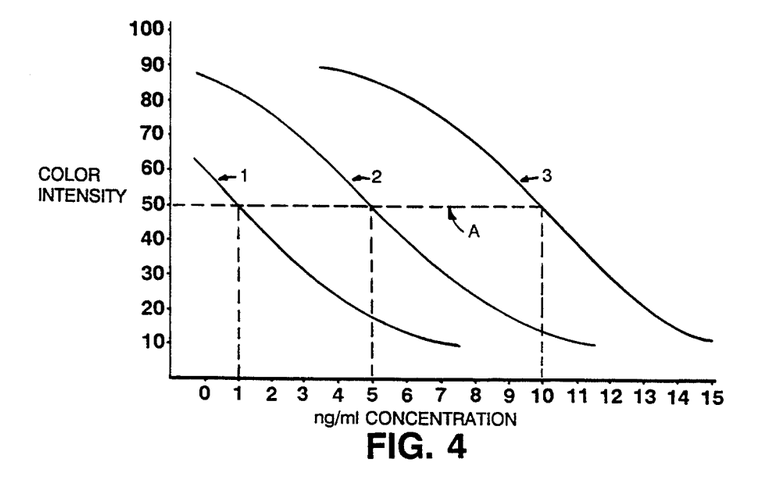
FIG. 4 is a graph illustrating the response of the three test areas of the support of FIG. 2 to varying concentrations of a substance (equine progesterone).

The capacity of test spots one, two and three to react differently to the same concentration of progesterone is illustrated in FIG. 4, which shows that, for each spot, a different concentration of progestrone in the sample is required to produce a linear decrease in color intensity. FIG. 4 shows that test spot one contains sufficient antibody such that the color intensity drop from fifty to twenty units is substantially linear over a concentration of one to five ng/ml of progestrone; the color intensity drop from fifty to twenty units of test spot two is substantially linear over a progestrone concentration of between five and ten ng/ml; and a color intensity drop from fifty to twenty units for test spot three is substantially linear for progestrone concentrations between ten and fifteen ng/ml.

Thus comparison of the color intensity of the test spots with that of the reference spot provides a semiquantitative indication of the amount of progesterone in the test sample. This is of great importance for this hormone, because its level serves as an indication of estrus and also of maintenance of pregnancy in horses. In the case of a pregnant mare, a serum progesterone level above about 4 ng/ml indicates that pregnancy is being maintained, while a level below 4 ng/ml indicates that there may be a problem with pregnancy maintenance, and corrective action may be required. In the case of a mare which is not pregnant, a serum progesterone level below about 1 ng/ml indicates estrus, i.e., that the mare is ready for breeding. In addition to these general principles, because every mare has its own distinctive physiology, it is important, for any given breeding mare, to follow progesterone levels over time, to obtain a historical profile of the hormone cycling of that mare, so that impregnation and pregnancy maintanence can be optimized.

As mentioned above, the test spots can contain progesterone rather than antibody, in which case labeled antibody to progesterone is used.

Operation of Single Spot Competitive Assay

Where membrane 18 bears only one test spot, containing progesterone or anti-progesterone antibody in an amount such that it undergoes significant color change only when the progesterone level in the sample is above a physiologically significant level, the assay is carried out as described above, except that membrane 18 bears only one test spot.

Sandwich Immunoassay Apparatus

Figure 5:
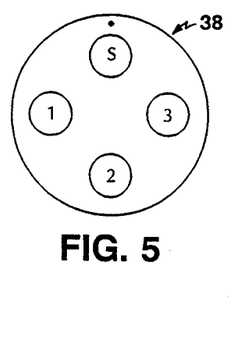
FIG. 5 is a diagrammatic representation of a membrane for use in a sandwich immunoassay of the invention.

The apparatus illustrated in FIGS. 1A and 1B is also used in the sandwich assay, except that membrane 18 is replaced by membrane 38, shown in FIG. 5. Membrane 38 is adapted to provide a semiquantitative measure of equine IgG in foal serum. The apparatus, including membrane 38, is commercially available from Agritech Systems, Inc., 100 Fore Street, Portland, Me., and is sold under the trademark CITE. Spot S on membrane 38, located below orientation dot 40, comprises latex particles coated with antibody to equine IgG (Jackson Immunoresearch, P.O. Box 683, Avondale, Pa.). Calibration spots 1, 2, and 3 contain no anti-IgG antibody, but do contain, respectively, horse IgG equivalent to the amount captured by spot S from a 200 mg/dl, 400 mg/dl, and 800 mg/dl sample, coated on latex particles. Antibody to equine IgG, which is also commercially available from a number of sources, is loaded onto the latex particle as described above for equine progesterone.

Operation of Semiquantitative Sandwich Assay

The apparatus of FIGS. 1A and 1B, including membrane 38, is used in conjunction with serum, plasma, or anti-coagulated whole blood samples, drawn from foals. Because of variations in hematocrit among foals, it is most preferable to use serum or plasma, which can either be fresh or previously frozen. If whole blood is used, it must, prior to assay, be anti-coagulated with heparin, EDTA, or citrate. Hemolyzed samples may be used without the risk of false positives.

Two microliters of serum or plasma from a foal are drawn into a microtiter capillary piper, and excess sample is wiped from the outside of the pipet. The sample is then inserted into a container containing standard phosphate buffer containing 5% BSA, as sample diluent, mixed, and ten drops of diluted sample are then added, via pipet, to the center of the assay apparatus of FIGS. 1A and 1B. The sample is permitted to react with membrane 38 for 3 minutes, after which time 4 drops of a solution containing a second anti-equine IgG antibody, conjugated to the enzyme alkaline phosphatase, are added. (Anti-equine IgG antibody conjugated with alkaline phosphatase is available from Jackson Immunoresearch, Avondale, Pa.) This second, labelled antibody binds to any equine IgG captured by reference spot S and also binds to that previously coated on spots 1, 2, and 3. The reaction is allowed to proceed for 2 minutes, after which time 5 to 10 drops of wash solution (composition described above) are added. Container 12 is then nearly filled with wash solution and, after the wash solution has been completely absorbed by absorbant 14 (at this point all of the blue color from the enzyme conjugate solution should be washed away), 4 drops of chromogenic substrate for alkaline phosphatase (indoxyl phosphate, JBL Scientific, California) are added. The substrate solution is allowed to stand for 3 minutes so that color may fully develop, after which time membrane 38 is inspected so that the IgG level in the sample can be determined.

Figure 6A:
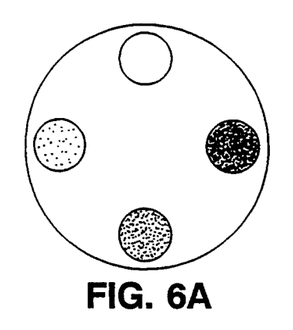
FIGS. 6A–6F are a diagrammatic representation of assay results obtained using the membrane of FIG. 5.
Figure 6B:
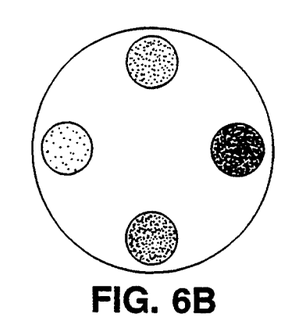
Figure 6C:
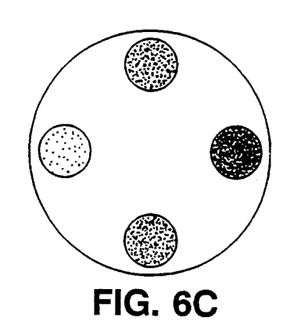
Figure 6D:
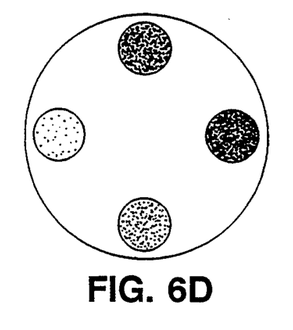
Figure 6E:
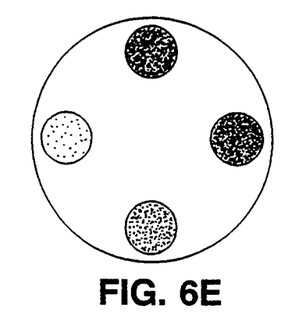
Figure 6F:
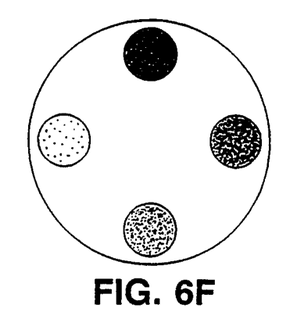

FIGS. 6A–6F illustrate the results obtained with six different concentrations of equine IgG. In each of the six membranes of 6A through 6F, calibration spots 1, 2, and 3 have reacted in the same way, i.e. spot 1, corresponding to 200 mg/dl IgG, is the lightest, spot 2, corresponding to 400 mg/dl, is next lightest, and spot 3, corresponding to 800 mg/dl, is the darkest of the three; the intensity of each spot, as explained above, is independent of IgG concentration in the sample, as the spots contain IgG, but no antibody to IgG. In the membrane of FIG. 6A, the sample spot remains white or is lighter in color than calibration spot 1, indicating that the sample contains less than 200 mg/dl equine IgG; in the membrane of FIG. 6B, the sample spot is darker than calibration spot 1 but lighter than calibration spot 2, indicating an IgG concentration of between 200 and 400 mg/dl; in the membrane of FIG. 6C, the sample spot is equal in color intensity to calibration spot 2, indicating an IgG concentration Of 400 mg/dl; in the membrane of FIG. 6D, the sample spot is darker than calibration spot 2 but lighter than calibration spot 3, indicating an IgG concentration of between 400 and 800 mg/dl; in membrane of FIG. 6E, the sample spot is equal in intensity spot 3, indicating an IgG concentration of 800 mg/dl; and in membrane of FIG. 6F, the sample spot is darker than calibration spot 3 indicating an IgG concentration of greater than 800 mg/dl.

The illustrated test is of great importance in the monitoring of the immune status of foals, which are born with little or no circulating immunoglobulin. Neonatal immunity to infectious agents requires the uptake and absorption of maternal antibodies from colostrum. Failure of passive transfer can occur as a result of premature lactation, deficient suckling, mal-absorption , or low levels of IgG in colostrum. Partial or complete failure of immune transfer occurs in 10 to 25 percent of all foals, and these animals are at high risk of serious illness or death. Greater than 800 mg of IgG per 100 ml serum is considered an adequate level of immunity. Levels of between 400 and 800 mg/dl may be adequate, but foals at this level are possibly at risk. IgG levels between 200 and 400 mg/dl reflect a partial failure of immune transfer, while concentrations of less than 200 mg/dl suggest total failure. Rapid identification of low IgG levels is essential to the early initiation of treatment of immunodeficient foals. Furthermore, post-treatment testing allows a timely evaluation of the success of IgG supplementation.

Semiquantative Sandwich Immunoassay Apparatus (Alternate Configuration)

Figure 7:
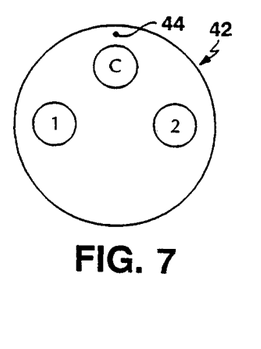
FIG. 7 is a diagrammatic representation of a membrane, for use in a sandwich immunoassay of the invention.

Referring to FIG. 7, an alternate semiquantative immunoassay employs the apparatus of FIGS. 1A and 1B, and in place of membrane 38 (FIG. 5) described above, membrane 42, which bears orientation dot 44, positive control spot C, and test spots 1 and 2; membrane 42 is adapted to be used to estimate IgG levels in foal serum. Test spot 1 contains about 60% latex particles coated with anti-equine IgG antibody (the other 40% are BSA-coated particles), while test spot 2 contains about 5% antibody-coated latex particles. Because of the high concentration of antibody on spot 1, favorable reaction kinetics will apply, and a substantial (greater than 50% of the potential) color reaction will develop even in the presence of less than 400 mg/dl IgG. Because of the unfavorable reaction kinetics resulting from the low antibody concentration on spot 2, a sample IgG concentration below 400 mg/dl will not develop substantial color, and a higher concentration is required for such development.

Positive control spot C contains no antibody to foal IgG but only latex particles coated with antibody to HRP; the only function of spot 34 is to serve as an indicator that the chromogenic system is operative (absence of color in spot 34 indicates a defective assay).

Operation of Alternate Sandwich Immunoassay

The alternate sandwich immunoassay is carried out as described above for equine IgG, except that membrane 42 (FIG. 7) is used in place of membrane 38.

Figure 8A:
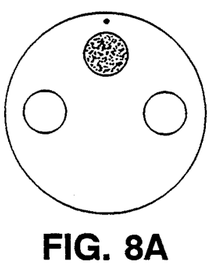
FIGS. 8A–8C are a diagrammatic representation of assay results obtained using the membrane of FIG. 7.
Figure 8B:
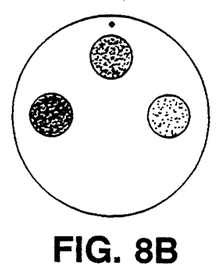
Figure 8C:
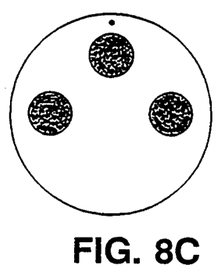

Typical results of the assay are shown in FIGS. 8A–8C. In all 3 membranes of FIGS. 8A, 8B and 8C the positive control spot C bears a dark color, indicating that the assay reagents are operative. In the membrane of FIG. 8A, neither of test spots 1 and 2 has developed color, indicating the absence in the sample of foal IgG. In the membrane of FIG. 8B, test spot 1, which is heavily loaded with antibody, has developed a dark color, but test spot 2, bearing less antibody, has developed only a slight amount of color, indicating that some low level, e.g. on the order of <400 mg/dl, of IgG is present in the sample. In the membrane of FIG. 8C, both test spots 1 and 2 have developed a dark color, indicating that the sample contains a high concentration, e.g., above 400 mg/dl, of IgG.

Other Embodiments

Other embodiments are within the following claims. For example, in any of the above assays in which there are multiple reference, test, or calibration spots, there may be more spots than are illustrated in the examples. In addition, one support membrane can bear antigen or antibody appropriate for measurement of more than one analyte, so that, for example, two or more drugs, toxins, proteins, or antibodies can be detected all at the same time. Any of a variety of labels can be used, including machine-readable signal generating systems such as radioiostopes, although enzyme-chromogen systems are most preferred because they obviate the use of instrumentation for the reading of results. Membranes can be made of other natural or synthetic fibers, e.g., nylon.

We claim:

1. A kit for the semi-quantitative measurement of an analyte in a liquid sample by competitive immunoassay, said analyte comprising a first member of a specific binding pair, said specific binding pair comprising a first member and second member which specifically bind to each other, said kit comprising a solid support bearing:

a first test area exposed to receive sample, said first test area comprising a first amount of at least one member of said specific binding pair, said first test area producing a first signal in said immunoassay responsive to analyte in said sample;

a second test area exposed to receive sample, said second test area comprising a second amount of at least one member of said specific binding pair, said second test area producing a second signal in said immunoassay responsive to the amount of said analyte in said sample, said second signal being of an intensity different from the intensity of said first signal for a given amount of analyte in said sample; and a reference area which provides u reference signal of predetermined detectable intensity in said immunoassay independent of the amount of said analyte in said sample, said reference area comprising a reactant which reacts with a labeled component used in said immunoassay to provide said reference signal, said reactant being present in an amount to provide said reference signal, said reference signal being of an intensity related quantitatively to the intensities of each of said signal levels generated by each of said test areas in the presence of a predetermined standard analyte level, according to the following relationship the intensity of said reference signal is distinguishably above the intensity of the signal from one of said test spots and distinguishable below the intensity of the signal from the other test spot;

whereby the intensity of the signal from said reference area can be compared with the intensity of signals from each of said test areas in the presence of an unknown quantity of the analyte in said sample to determine the amount of said analyte in said sample relative to said predetermined standard analyte level.

2. The kit of claim 1 wherein said first test area and said second test comprise the same member of said specific binding pair, and said first amount is different from said second amount, said first amount and said second amount are selected so that said first area, but not said second area, generates a detectable signal of lower intensity than that of said reference area when said sample contains a first concentration of said analyte, and both said areas generate detectable signals lower in intensity than that of said reference area when said sample contains a second concentration of said analyte, greater than said first concentration, of said analyte.

3. The kit of claim 2 further comprising a container of a solution comprising a labeled member of said specific binding pair present in an amount suitable for competitively binding to the pair member in said test areas, binding of said labeled member of said test area being inverse to the amount of said analyte in said sample.

4. The kit of claim 3 wherein said first test area and said second test area each comprise said second member of said specific binding pair immobilized on said support, and said kit further comprises said first member of said binding pair labeled with an enzyme, and said reference area comprises antibody to said enzyme, said reference area being free from said molecules that specifically bind said first member of said specific binding pair,
whereby said competitive immunoassay is an enzyme immunoassay in which enzyme labeled first member of said specific binding pair competes with first member of said specific binding pair present in said sample for binding to the second member of said specific binding pair in said first test area and in said second test area.

5. The kit of claim 4 wherein said second member of said binding pair is immobilized in said first test area in an amount that is saturated by said first member in said sample when said sample contains said first member of said specific binding pair in a first amount; and said second member of said binding pair is immobilized in said second test area in an amount that is not saturated by said first member in said sample when said sample contains said member of said specific binding pair in said first amount, but is saturated by said first member in said sample when it is present in a second, higher amount.

6. The kit of claim 3 wherein said first test area and said second test area each comprise said first member of said binding pair immobilized on said support and said kit further comprises said second member labeled with an enzyme, and said reference area comprises antibody to said enzyme, and is free from said first member of said binding pair,
whereby said competitive immunoassay is an enzyme immunoassay in which the first member of said specific binding pair immobilized on said support competes with the first member of said specific binding pair in said sample for binding to the enzyme-labeled second member of said specific binding pair, in said first test area and in said second test area.

7. The kit of claim 1 wherein the intensity of the signal generated by said first test area varies in substantially linear fashion when said sample contains said first member of said specific binding pair in an amount within a first range, and the intensity of the signal generated by said second test area varies in substantially linear fashion when said sample contains said first member of said specific binding pair in an amount within a second, greater range.

8. The kit of claim 1 wherein said first member of said specific binding pair is a hormone.

9. The kit of claim 8 wherein said hormone is equine progesterone.

10. The kit of claim 1 wherein said first signal is a visible signal, said second signal is a visible signal of about the same color as said first signal, and said reference signal is a visual signal of about the same color as said first signal and said second signal.

11. A method of semiquantitative measurement of an analyte in a liquid sample by competitive immunoassay to determine the amount of said analyte in said sample relative to a predetermined standard analyte level, said analyte comprising a first member of a specific binding pair, said specific binding pair comprising said first member and a second member which specifically bind to each other, said method comprising
1) providing a solid support comprising
   a first test area exposed to receive sample, said first test area comprising a first amount of at least one member of said specific binding pair, said first test area producing a first signal in said immunoassay responsive to analyte in said sample,
   a second test area exposed to receive sample, said second test area comprising a second amount of at least one member of said specific binding pair, said second test area producing a second signal in said immunoassay responsive to the amount of said analyte in said sample, said second signal being of an intensity different from the intensity of said first signal for a given amount of analyte in said sample; and
   a reference area which provides a reference signal of predetermined detectable intensity in said immunoassay independent of the amount of said analyte in said sample, said reference area comprising a reactant which reacts with a labeled component used in said immunoassay to provide said reference signal, said reactant being present in an amount to provide said reference signal, said reference signal being of an intensity related quantitatively to the intensities of each of said signal levels generated by each of said test areas in the presence of a predetermined standard analyte level, according to the following relationship:
      the intensity of said reference signal is distinguishably above the intensity of the signal from one of said test spots and distinguishable below the intensity of the signal from the other test spot;
2) contacting said solid support with said liquid sample and with enzyme-labeled first member, if said support bears second member, or enzyme-labeled second member, if said support bears said first member, to produce said detectable signals and said reference signal; and
3) comparing the signal intensity of each said test area to that of said reference area to determine the amount of said analyte in said sample relative to said standard analyte level.

* * * * *

UNITED STATES PATENT AND TRADEMARK OFFICE
CERTIFICATE OF CORRECTION

Page 1 of 2

PATENT NO. : 5,356,785
DATED : October 18, 1994
INVENTOR(S) : McMahon et al

It is certified that error appears in the above-indentified patent and that said Letters Patent is hereby corrected as shown below:

On the cover page: Item [54] and Column 1, line 2, insert an --A-- after the word "and".

Cover page: Other Publications: - delete the word "Their" in title and insert the word "the".

Column 1 - line 2 - insert and "A" after the word "and".

Column 2 - line 13 - underline number 72.

Column 5 - line 12 - insert an "A" after "#1."

Column 5 - line 17 - insert "of" after "concentrations".

UNITED STATES PATENT AND TRADEMARK OFFICE
CERTIFICATE OF CORRECTION

PATENT NO. : 5,356,785
DATED : October 18, 1994
INVENTOR(S) : McMahon et al

It is certified that error appears in the above-indentified patent and that said Letters Patent is hereby corrected as shown below:

Column 6 - line 35 - delete the "s" after the "e" in the word illustrates.

Column 6 - line 41 - delete "A of FIG 3", insert "of Fig. 3A".

Column 6 - line 60 - delete "F" after #3 amd insert "G".

Column 8 - line 7 - deleter "r" and insert a "t" in the word pipet.

Column 9 - line 48,- insert a comma after 8C.

Column 10 - line 31 - delete "u" after provides and insert an "a".

Signed and Sealed this

Twentieth Day of August, 1996

Attest:

BRUCE LEHMAN

Attesting Officer      Commissioner of Patents and Trademarks